US012150759B2

(12) United States Patent
Workman et al.

(10) Patent No.: US 12,150,759 B2
(45) Date of Patent: *Nov. 26, 2024

(54) BLOOD-SOLUTE CALCULATION WITH A MOBILE DEVICE USING NON-INVASIVE SPECTROSCOPY

(71) Applicant: Google LLC, Mountain View, CA (US)

(72) Inventors: Christopher David Workman, Mountain View, CA (US); Ricky Bomber, Sunnyvale, CA (US); Kelly Dobson, Mountain View, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/302,569

(22) Filed: Apr. 18, 2023

(65) Prior Publication Data

US 2023/0263436 A1     Aug. 24, 2023

Related U.S. Application Data

(63) Continuation of application No. 16/959,509, filed as application No. PCT/US2019/021562 on Mar. 11, 2019, now Pat. No. 11,660,027.

(Continued)

(51) Int. Cl.
*A61B 5/1455* (2006.01)
*A61B 5/00* (2006.01)
(Continued)

(52) U.S. Cl.
CPC .......... *A61B 5/1455* (2013.01); *A61B 5/6803* (2013.01); *A61B 5/681* (2013.01);
(Continued)

(58) Field of Classification Search
CPC ... A61B 5/1455; A61B 5/7257; A61B 5/7267; A61B 5/14551
See application file for complete search history.

(56) References Cited

U.S. PATENT DOCUMENTS 5,440,388 A    8/1995   Erickson
5,747,806 A    5/1998   Khalil et al.
(Continued)

FOREIGN PATENT DOCUMENTS

WO     2019177941     9/2019

OTHER PUBLICATIONS

"International Preliminary Report on Patentability", Application No. PCT/US2019/021562, Sep. 24, 2020, 10 pages.

(Continued)

*Primary Examiner* — Eric F Winakur
(74) *Attorney, Agent, or Firm* — Colby Nipper PLLC

(57) ABSTRACT

This document describes techniques and devices for blood-solute calculation with a mobile device using non-invasive spectroscopy. A mobile device (502) includes a light source (504) that emits light toward an interferometer (508) that uses mirrors to separate and recombine the light. The interferometer directs the recombined light toward a person. Light reflected from, or transmitted through, the person is received through a reception port (506) to a photodetector (510) that outputs photodetector data that corresponds to a measured light intensity of the reflected and transmitted light as a function of a path length of the light or a mirror position of the interferometer. Based on the photodetector data, an interferogram is generated. Applying a technique such as a Fourier transform to the interferogram, a spectrum data set of the reflected and transmitted light is generated. Based on the spectrum data set, a concentration of solutes in the person's blood is calculated.

20 Claims, 12 Drawing Sheets

Related U.S. Application Data

(60) Provisional application No. 62/642,988, filed on Mar. 14, 2018.

(51) Int. Cl.
    *G01J 3/02* (2006.01)
    *G01J 3/453* (2006.01)
    *A61B 5/145* (2006.01)

(52) U.S. Cl.
    CPC .......... *A61B 5/6898* (2013.01); *A61B 5/7257* (2013.01); *A61B 5/7267* (2013.01); *G01J 3/0272* (2013.01); *G01J 3/4532* (2013.01); *A61B 5/14532* (2013.01); *A61B 5/14546* (2013.01); *A61B 2562/0238* (2013.01); *G01J 2003/4534* (2013.01)

(56) References Cited

U.S. PATENT DOCUMENTS

| | | | |
|---|---|---|---|
| 6,728,571 | B1 | 4/2004 | Barbato |
| 7,526,329 | B2 | 4/2009 | Hogan et al. |
| 8,175,665 | B2 * | 5/2012 | Baker, Jr. ............. A61B 5/0059 600/310 |
| 10,912,502 | B2 | 2/2021 | Poeze et al. |
| 10,945,648 | B2 | 3/2021 | Poeze et al. |
| 11,660,027 | B2 | 5/2023 | Workman et al. |
| 2005/0267346 | A1 | 12/2005 | Faber et al. |
| 2012/0098924 | A1 | 4/2012 | Busch et al. |
| 2012/0274934 | A1 | 11/2012 | Messerschmidt |
| 2013/0215042 | A1 | 8/2013 | Messerschmidt et al. |
| 2016/0054179 | A1 | 2/2016 | Carr |
| 2017/0164878 | A1 | 6/2017 | Connor |
| 2017/0363469 | A1 | 12/2017 | Sabry et al. |
| 2020/0390372 | A1 | 12/2020 | Workman et al. |

OTHER PUBLICATIONS

"International Search Report and Written Opinion", Application No. PCT/US2019/021562, Jun. 26, 2019, 16 pages.

"Non-Final Office Action", U.S. Appl. No. 16/959,509, filed Jun. 24, 2022, 6 pages.

"Notice of Allowance", U.S. Appl. No. 16/959,509, filed Feb. 1, 2023, 7 pages.

\* cited by examiner

300-A

300-B

BLOOD-SOLUTE CALCULATION WITH A MOBILE DEVICE USING NON-INVASIVE SPECTROSCOPY

CROSS-REFERENCE TO RELATED APPLICATION(S)

This application is a continuation of and claims priority to U.S. Non-Provisional patent application Ser. No. 16/959,509, filed on Jul. 1, 2020, which is a National Stage Entry of International Application No. PCT/US2019/021562, filed on Mar. 11, 2019, which in turn claims priority to U.S. Provisional Patent Application Ser. No. 62/642,988, filed on Mar. 14, 2018, the disclosures of which are incorporated by reference herein in their entireties.

BACKGROUND

Wearable technology, like smartwatches and computing glasses, is increasingly common. One popular type of wearable is a fitness indicator, such as a smartwatch. Wearable fitness indicators can provide reminders about activities, such as how many steps a wearer takes or how long the wearer has been sitting down. Wearable fitness indicators can also measure various biological parameters that are associated with health or fitness, such as heart rate and blood-oxygen level.

Much of the information that can be used to provide health indications, however, cannot be measured with most wearable technology because the information is accessible only by analyzing a person's internal biology. For example, some of the most useful and important information about a person's health and fitness is determined from measurements of solutes in the person's blood, such as blood-glucose, total hemoglobin, lactate, or blood-alcohol. Blood-glucose level measurements are used to determine frequency and dosage of insulin for people with diabetes. Similarly, total hemoglobin levels can be used to diagnose and monitor anemia. In addition to disease monitoring and health indications, blood-solute measurements can be used for fitness training and to encourage responsible behavior. For example, a measurement of lactate levels can be used to help an athlete train to improve endurance, and a measurement of blood-alcohol concentration can be used to determine whether a person should drive.

Often, this useful information goes unmeasured because of the invasiveness or complexity of the process used to collect the information. People with diabetes, for instance, typically measure their blood-glucose concentration several times per day using a fingerstick method (piercing the skin on a finger to provide a small blood sample) or by wearing a continuous glucose monitor that is inserted under the skin. Similarly, those suffering from anemia also regularly provide blood samples via a fingerstick or by visiting a healthcare provider to have blood drawn. The unavailability, pain, or inconvenience of these methods may cause some people to forgo a test and possibly damage their health.

This background description is provided for the purpose of generally presenting the context of the disclosure. Unless otherwise indicated herein, material described in this section is neither expressly nor impliedly admitted to be prior art to the present disclosure or the appended claims.

SUMMARY

This document describes techniques and devices for blood-solute calculation with a mobile device using non-invasive spectroscopy. The mobile devices include a light source that emits light toward an interferometer that uses mirrors to separate and recombine the light. The interferometer directs the recombined light toward a subject, in particular a living being, such as a person. Light reflected from, or transmitted through, the subject is received through a reception port to a photodetector that outputs data that corresponds to a measured light intensity of the reflected and transmitted light as a function of a path length of the light or a mirror position of the interferometer. Based on the data from the photodetector, an interferogram is generated. Applying a mathematical technique such as a Fourier transform to the interferogram, a spectrum data set of the recombined light can be generated. Based on the spectrum data set, a concentration of solutes in the person's blood can be calculated.

A processor in the mobile device can use the detector data to generate an interferogram and then compute the Fourier transform of the interferogram to generate a spectrum data set of the wavelengths of light reflected from, transmitted through, and absorbed by, the subject. Knowing the original intensity as a function of wavelengths transmitted, the wavelengths that are absent (absorbed) and present (not absorbed) in the spectrum data set can be used to describe the molecules in the person's tissues. Using a technique such as partial least squares (PLS) regression, the spectrum data set can be used to determine concentrations of solutes in the person's blood.

Aspects described below include a mobile computing device comprising a light source disposed at least partially within a housing and configured to emit light toward an interferometer disposed at least partially within the housing. The interferometer receives the emitted light and separates and recombines the emitted light at varied optical path lengths. The interferometer also directs the recombined light toward a person. The mobile computing device also includes a reception port disposed at least partially within the housing, which can collect reflected light. The reflected light includes emitted light that is reflected from, or transmitted through, the person. The mobile computing device also includes a photodetector disposed at least partially within the housing. The photodetector can receive the reflected or transmitted light and output detector data that corresponds to a measured light intensity of the reflected light as a function of a path length or a mirror position of the interferometer. The mobile computing device further includes a spectroscopy module that can generate, based on the detector data, an interferogram. The spectroscopy module also generates, based on the interferogram, a reflectance spectrum data set or a transmittance spectrum data set of the reflected light. Additionally, the spectroscopy module calculates a concentration of one or more solutes in the person's blood based on the reflectance spectrum data set, the transmittance spectrum data set, or an absorbance spectrum data set.

Aspects described below also include a method. The method comprises emitting light from a light source disposed at least partially within a housing, the light emitted toward an interferometer disposed at least partially within the housing and configured to separate and recombine, at varied optical path lengths, the emitted light. The method also includes directing, by the interferometer, the recombined light toward a person. The method additionally includes receiving, by a photodetector disposed at least partially within the housing, reflected or transmitted light, the reflected or transmitted light reflected from, or transmitted through, the person. The method further includes outputting, by the photodetector, detector data that corresponds to a measured light intensity of the reflected or transmitted light as a function of a path length or a mirror position of the interferometer. The method also includes generating, based on the detector data, an interferogram and generating, based on the interferogram, a reflectance spectrum data set or a transmittance spectrum data set of the reflected light. The method additionally includes calculating a concentration of one or more solutes in the person's blood, based on the reflectance spectrum data set, the transmittance spectrum data set, or an absorbance spectrum data set.

Aspects described below also include another method. The method comprises emitting light, from a light source disposed at least partially within a housing, toward a person. The method also includes collecting, at a reception port disposed at least partially within the housing, reflected light from the light source, the reflected light reflected from, or transmitted through, the person. The method additionally includes separating and recombining, by an interferometer disposed at least partially within the housing, the collected light at varied optical path lengths. The method further includes receiving, by a photodetector disposed at least partially within the housing, the recombined light. The method also includes outputting, by the photodetector, detector data that corresponds to a measured light intensity of the recombined light as a function of a path length or a mirror position of the interferometer. The method additionally includes generating, based on the detector data, an interferogram and generating, based on the interferogram, a reflectance spectrum data set or a transmittance spectrum data set of the recombined light. The method further includes calculating a concentration of one or more solutes in the person's blood, based on the reflectance spectrum data set, the transmittance spectrum data set, or an absorbance spectrum data set.

Aspects described below also include another method. The method comprises emitting light from a light source disposed at least partially within a housing, the light emitted toward a first means disposed at least partially within the housing and configured to separate and recombine the emitted light at varied optical path lengths. The method also includes directing the recombined light, by the first means, toward a person. The method additionally includes receiving, by a photodetector disposed at least partially within the housing, reflected or transmitted light, the reflected or transmitted light reflected from, or transmitted through, the person. The method further includes outputting, by the photodetector, detector data that corresponds to a measured light intensity of the reflected light as a function of an operating parameter of the first means. The method also includes a second means that can be used for generating, based on the detector data, an interferogram and generating, based on the interferogram, a reflectance spectrum data set or a transmittance spectrum data set of the reflected light. The method additionally includes a third means that can be used for calculating a concentration of one or more solutes in the person's blood, based on the reflectance spectrum data set, the transmittance spectrum data set, or an absorbance spectrum data set. The methods may be carried out using any of the mobile devices described above.

This summary is provided to introduce simplified concepts related to blood-solute calculation with a mobile device using non-invasive spectroscopy, the concepts are further described below in the Detailed Description. This summary is not intended to identify essential features of the claimed subject matter, nor is it intended for use in determining the scope of the claimed subject matter.

BRIEF DESCRIPTION OF THE DRAWINGS

The details of one or more aspects of blood-solute calculation with a mobile device using non-invasive spectroscopy are described in this document with reference to the following drawings. The same numbers are used throughout the drawings to reference like features and components.

DETAILED DESCRIPTION

Overview

This document describes techniques using, and devices enabling, blood-solute calculation with a mobile device using non-invasive spectroscopy. Through use of these techniques and devices, a person can determine concentrations of blood solutes, which can be used to determine whether the person should take (or delay taking) medicine, see a medical professional, or change an activity or behavior. For many people, the ability to noninvasively and painlessly obtain this kind of information makes them more likely to act to maintain or improve their health. Additionally, these techniques may make treatment of some medical conditions available in areas where there is less access to conventional methods. Considering that worldwide, over 400 million people have diabetes and over 1.5 billion people are anemic, wide application of these techniques can improve the health and quality of life of hundreds of thousands of people and may potentially save many lives.

Consider, for example, a case in which a child has Type I diabetes and must monitor blood-glucose concentrations several times per day. For each measurement, the child produces a small blood sample (e.g., by a "fingerstick" process—piercing the skin on a finger and squeezing out a drop of blood) and applies the sample to a test strip. The test strip is then inserted into a blood-glucose meter, which measures and displays the child's blood-glucose level. Alternatively, the child can use a continuous glucose monitor by having a disposable glucose sensor implanted under the skin. The sensor monitors glucose levels in interstitial fluid and uses a wireless communication signal to transmit measurements to a receiving device. The sensor can be worn for a few days and then replaced with a new sensor. The sensor is typically calibrated once or twice a day via a blood sample. With either the sample-strip method or continuous monitoring, the child will have to provide blood at least twice a day, and up to eight or even ten times per day.

In contrast, using the described techniques, the child can wear a fitness indicator, such as a smartwatch, to noninvasively measure blood-glucose levels, without a fingerstick. In this way, the described techniques enable the child or a caregiver to monitor the child's blood-glucose levels to manage Type I diabetes without stopping several times a day to perform a sometimes-painful blood test.

This is merely one simple example of ways in which blood-solute calculation with a mobile device using non-invasive spectroscopy may be used, other examples and details are provided below. This document now turns to an example environment, after which example devices and methods, as well as an example computing device, are described.

Example Environment

Figure 1:
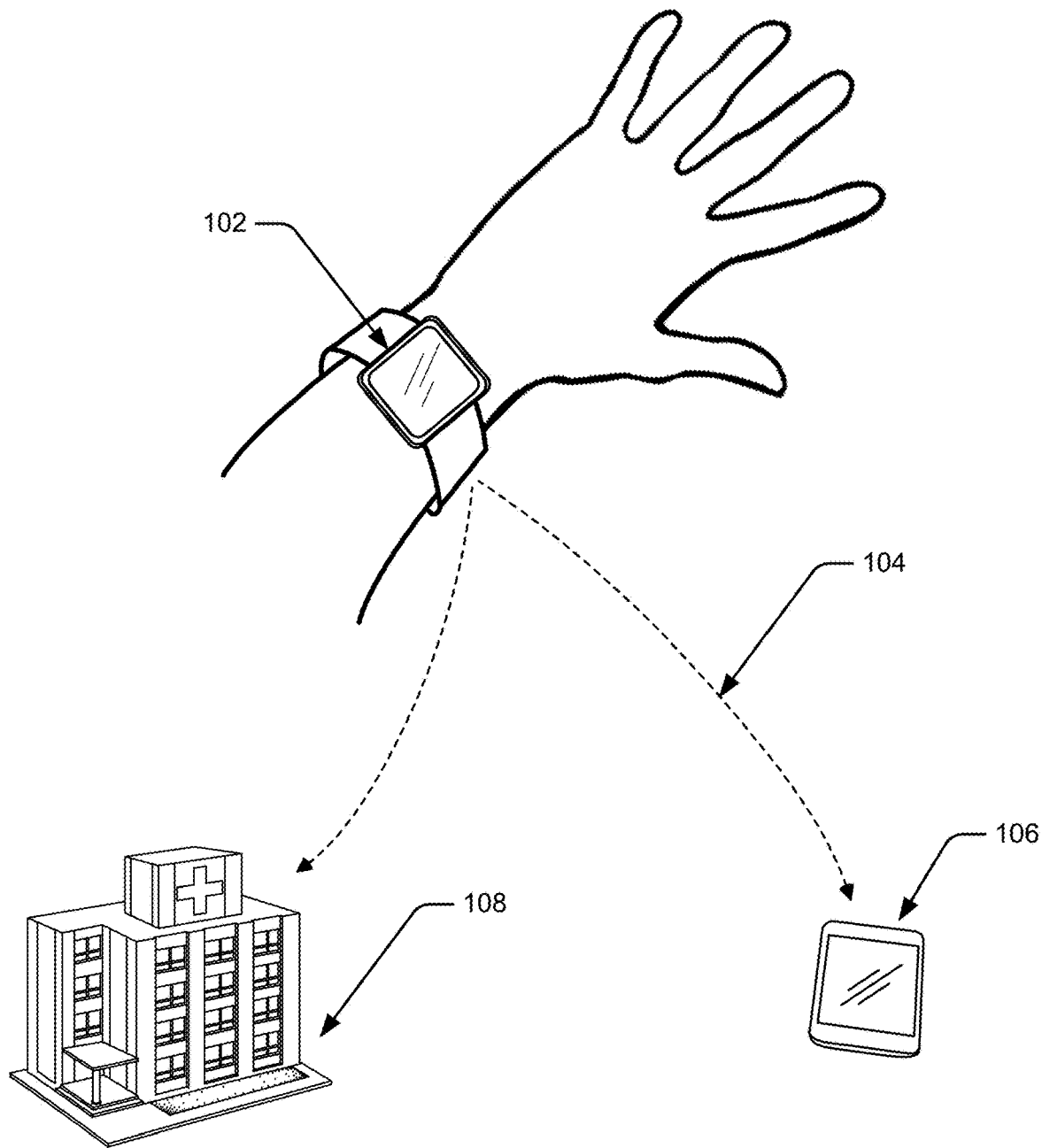
FIG. 1 illustrates an example environment in which techniques enabling blood-solute calculation with a mobile device using non-invasive spectroscopy can be implemented.

FIG. 1 illustrates an example environment 100 in which blood-solute calculation with a mobile device using non-invasive spectroscopy can be implemented. The example environment 100 illustrates a mobile device 102 that can be used to perform FT-IR spectroscopy. In the example, the mobile device 102 is a smartwatch device worn on a wrist of a person that is the subject of the spectroscopic analysis. In other examples, the smartwatch may be worn at another location, such as around an ankle, or the mobile device 102 may be another kind of device, such as eyewear, a ring, or a smartphone. Other configurations of the mobile device 102 are illustrated in later figures.

The mobile device 102 generates detector data 104 that can be used to determine a concentration of various solutes in the person's blood or other tissue (e.g., intracellular fluid or extracellular fluid). The concentration of solutes determined using the detector data 104 can include, for example, concentrations of glucose, hemoglobin, sodium, lactate, or ethyl alcohol. The detector data 104 is communicable from the mobile device 102 to other entities, such as a smartphone 106, a healthcare provider 108, or some other computing device remote from the person (not shown). Thus, the determination of the concentration of solutes can be performed by the mobile device 102 or one of the other entities. Once determined, the concentration of solutes can be displayed on a user interface of the mobile device 102, on a display of the smartphone 106, or at the healthcare provider 108.

Consider an example in which the mobile device 102 is used to measure a person's blood-glucose level at a particular instant in time. The person may be knowledgeable regarding whether and how to respond to the particular concentration measurement. For example, based on the displayed concentration of blood-glucose, the person may know whether to administer insulin (or wait to administer the insulin) or whether to eat or rest. In this case, the described techniques for blood-solute calculation with a mobile device using non-invasive spectroscopy are useful to help the person manage a condition like diabetes.

In another example, the person may be less knowledgeable about diabetes (e.g., a younger child or someone with a recent diagnosis). In this example, the mobile device 102 may be configured to determine blood-glucose concentrations at particular times and communicate the information to a third party, such as a teacher or the healthcare provider 108, who can advise the person (e.g., whether to eat or take insulin). Additionally or alternatively, the mobile device 102 may also include an application that can make treatment or behavioral recommendations to the person, based on the concentration measurement.

These and other capabilities and configurations are set forth in greater detail below. These entities may be further divided, combined, and so on. The environment 100 of FIG. 1 and the detailed illustrations of FIG. 2 through FIG. 11 illustrate some of many possible environments and devices capable of employing the described techniques.

Example Implementations

FIG. 2 through FIG. 11 depict example devices and techniques for implementing blood-solute calculation with a mobile device using non-invasive spectroscopy. These and other implementations are shown and described as techniques and operations performed but are not necessarily limited to the order or combinations in which the techniques and operations are shown. Further, any of one or more of the operations may be repeated, combined, reorganized, or linked to provide a wide array of additional and/or alternate methods. In portions of the following discussion, reference may be made to the environment 100 of FIG. 1 and as detailed in FIG. 2, reference to which is made for example only. The techniques are not limited to performance by one entity or multiple entities operating on one device.

Figure 2:
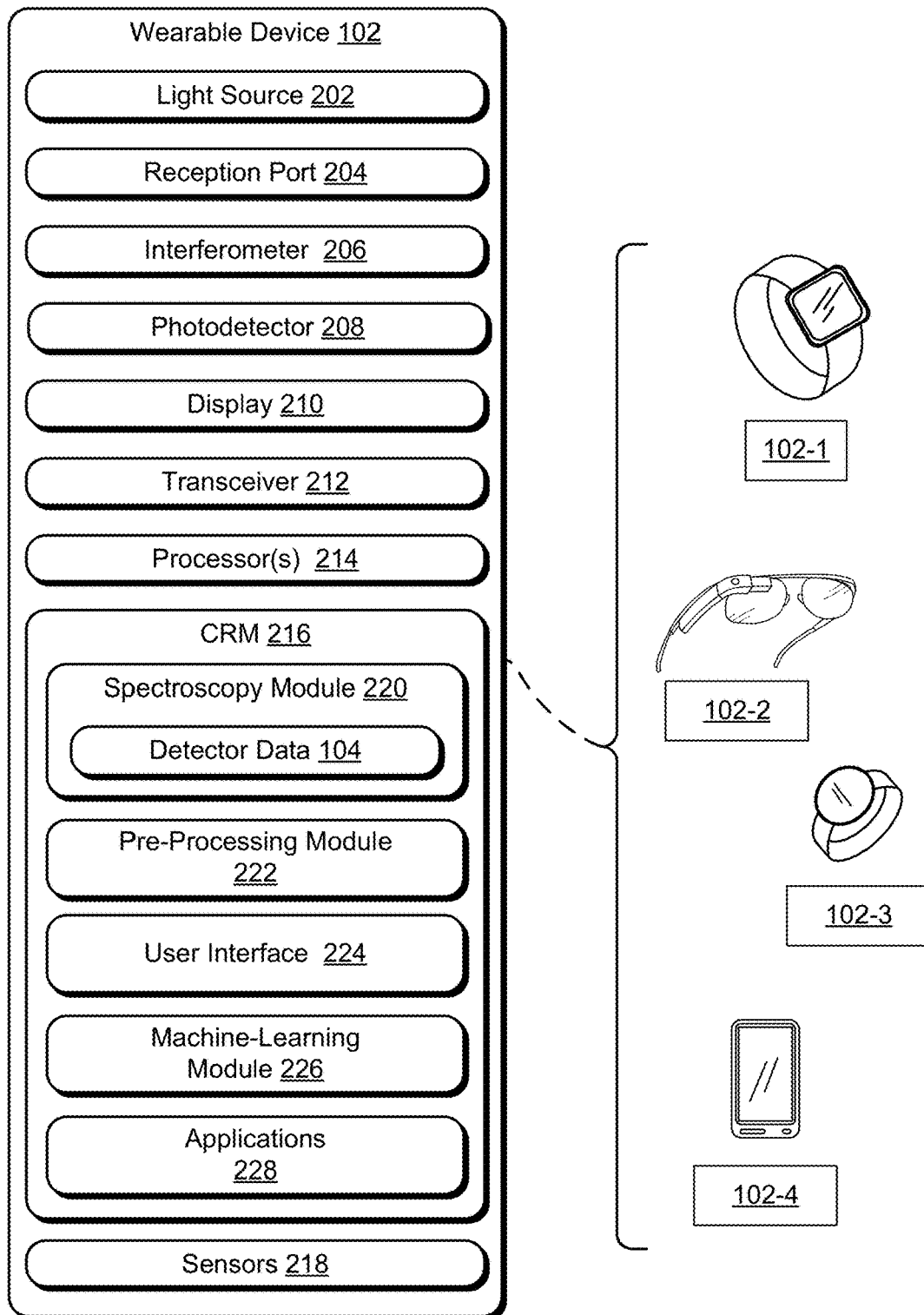
FIG. 2 illustrates an example implementation of the mobile device of FIG. 1 that includes an interferometer that can be used to generate a spectrum data set to implement aspects of blood-solute calculation with a mobile device using non-invasive spectroscopy.

With regard to the example mobile device 102 of FIG. 1, consider a detailed illustration in FIG. 2. The mobile device 102 can be one or a combination of various devices, here illustrated with four examples: a smartwatch 102-1, computing eyewear 102-2, a computing ring 102-3, and smartphone 102-4, though other mobile devices and systems, such as a dedicated personal FT-IR spectrometer may also be used. As noted above, in some implementations the techniques operate, at least in part, through a remote computing device. The remote computing device can be configured as a server, for example. In such cases, some computing and processing operations may not be performed locally, and the detector data 104 can be communicated to the remote device for determination of the solute concentrations. In this way, even devices that may have limited computing capacity can be used to implement the described techniques by transmitting the detector data 104 to another device that can determine the solute concentration.

The mobile device 102 includes a light source 202, a reception port 204, an interferometer 206, and a photodetector 208. The light source 202 is disposed at least partially within a housing of the mobile device 102 and can emit light toward a subject (e.g., the body or skin of a person using or wearing the mobile device 102). The light source 202 may be any of a variety of light sources that can emit broadband visible light and infrared (IR) light (e.g., electromagnetic (EM) radiation having wavelengths between approximately 100 nanometers (nm) and approximately 6000 nm). For example, the light source 202 may be a laser, a light-emitting-diode (LED), a laser diode, or a combination or array of diodes, laser diodes, and/or lasers. The reception port 204 is an opening in the housing of the mobile device 102 that collects reflected light and directs the reflected light to the interferometer 206. The reflected light includes light reflected from or transmitted through the subject. The reception port 204 may include optics (e.g., lenses or mirrors) that enable more-efficient collection of the reflected light.

The interferometer 206 is a miniaturized interferometer, such as a micro-electro-mechanical systems (MEMS) interferometer. The interferometer 206 can be any of a variety of configurations of interferometer that can be manufactured in a MEMS package, such as a Michelson interferometer, a Fabry-Perot interferometer, or a Twyman-Green interferometer. The interferometer 206 receives a beam of light (e.g., from a light source or light from the light source that is reflected from, or transmitted through, a subject such as a person) and uses mirrors to split the beam of light into two beams, introduce a phase difference between the two beams, and recombine the beams. In this way, the interferometer 206 can separate and recombine the emitted light at a varied optical path lengths. The interferometer 206 then directs the recombined light toward the subject or toward the photodetector 208.

In some implementations, one or more of the light source 202, the reception port 204, the interferometer 206, and the photodetector 208 may be provided as a printed circuit assembly (PCA). The PCA may also include other components, such as optical fiber conduits or electrical contacts for connecting the PCA to other components. In some cases the PCA may have exterior dimensions of approximately 15 millimeters (mm) by approximately 15 mm by approximately 4 mm. In other cases, the exterior dimensions may be different, (e.g., approximately 4 mm by approximately 4 mm by approximately 1 mm). These dimensions can enable the PCA to be integrated within mobile devices described herein, such as the smartwatch 102-1, the computing eyewear 102-2, the computing ring 102-3, the smartphone 102-4, and other computing devices and systems.

Figure 3:
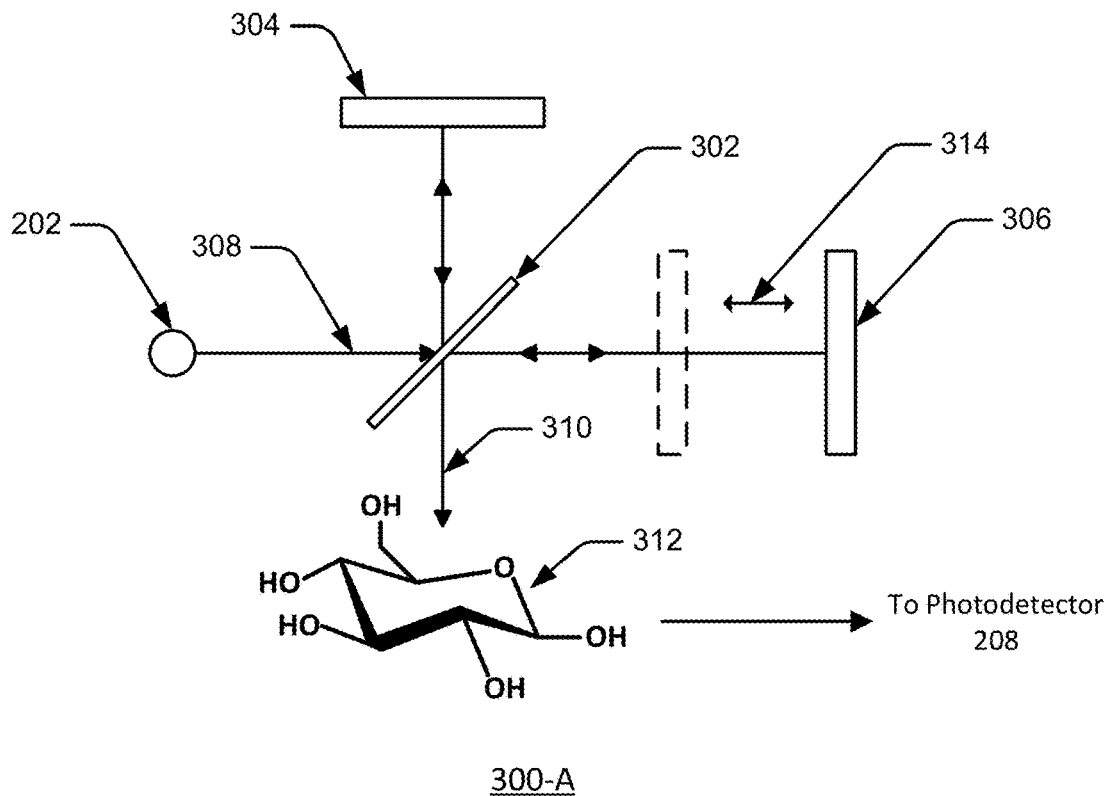
FIG. 3 illustrates two example implementations of the interferometer of FIG. 2.
Figure 3:
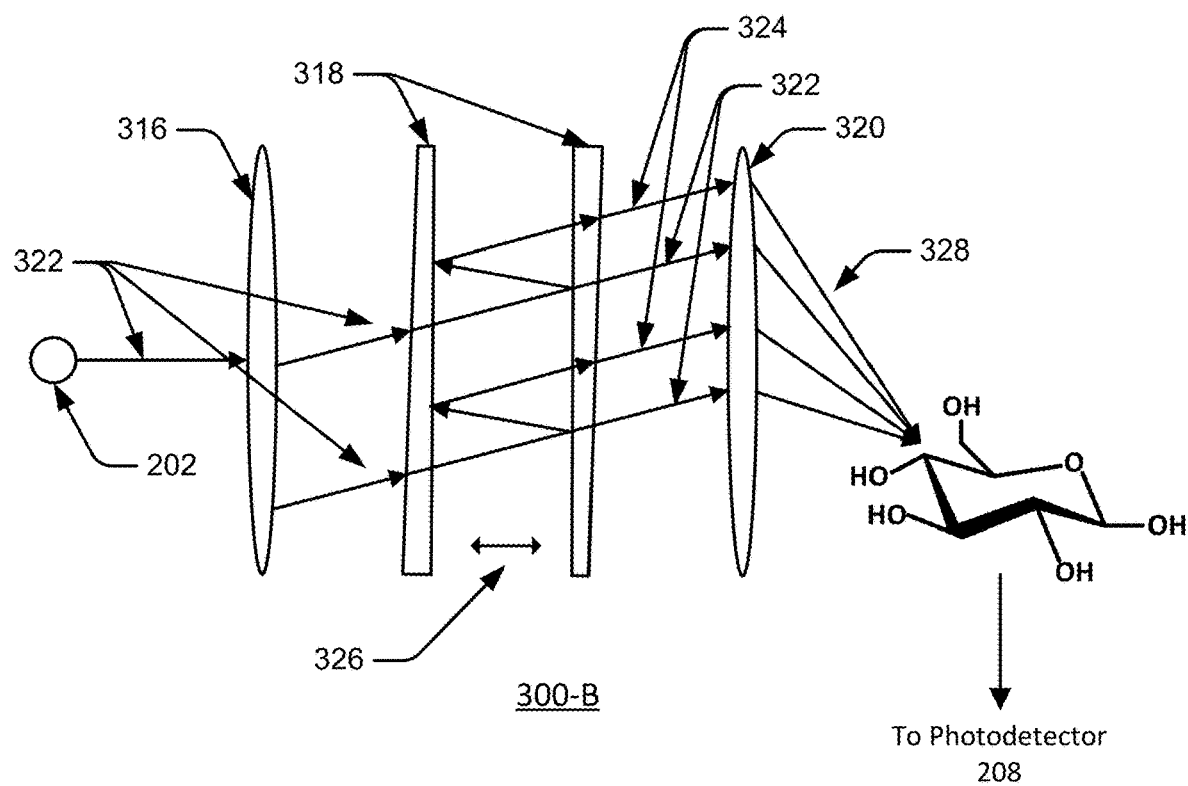

Consider FIG. 3, which describes two example configurations of the interferometer 206. Detail view 300-A illustrates an example Michelson interferometer. The example Michelson interferometer includes a beam splitter 302, a fixed mirror 304, and a moveable mirror 306. The beam splitter 302 splits a ray of light 308 emitted from a light source (e.g., the light source 202) into two beams and directs one beam toward the fixed mirror 304 and another beam toward the moveable mirror 306. The two beams reflected from the mirrors are recombined at the beam splitter 302. A recombined light beam 310 is directed out of the interferometer 206. The recombined light beam 310 can be directed toward a subject, shown as a skeleton formula representation of a glucose molecule 312. Portions of the recombined light 310 that are reflected from, or transmitted through, the subject are then received at a photodetector (e.g., the photodetector 208).

As the moveable mirror 306 changes position, as shown by arrow 314, the path length of the beam reflecting from the moveable mirror 306 changes, which introduces a phase difference between the two beams in the recombined beam 310. The phase difference causes wave interference, by which the multiple wavelengths of light in the beam are periodically blocked and transmitted. EM radiation at different wavelengths is modulated at different rates, so that at each moment, the recombined light (e.g., the recombined light beam 310) coming out of the example Michelson interferometer has a different spectrum.

Detail view 300-B illustrates an example Fabry-Perot interferometer. The example Fabry-Perot interferometer includes a collimating lens 316, a pair of partially reflective mirrors 318 with the reflective surfaces facing each other, and a focusing lens 320. The collimating lens 316, which may be omitted, can be used to align most or all rays of emitted light 322 that are emitted from a light source (e.g., the light source 202) to hit the partially reflective mirrors 318 at approximately the same angle. The partially reflective mirrors 318 may be rectangular or slightly wedge-shaped (as shown). One or both of the partially reflective mirrors 318 may be moveable. As the rays of the emitted light 322 pass between the partially reflective mirrors 318 the rays are reflected multiple times, which produces additional rays 324 for each original ray of emitted light 322. The additional rays 324 and the original rays of emitted light 322 are collected and recombined by the focusing lens 320.

As the distance between the partially reflective mirrors 318 changes, as shown by arrow 326, the path length of the additional rays 324 changes, which introduces a phase difference between the additional rays 324 and the original rays of emitted light 322. When the additional rays 324 and the original rays of emitted light 322 are recombined by the focusing lens 320, the phase difference causes wave interference, by which the multiple wavelengths of light in the beam are periodically blocked and transmitted. EM radiation at different wavelengths is modulated at different rates, so that at each moment, the recombined light 328 coming out of the example Fabry-Perot interferometer has a different spectrum. In either of the example interferometers shown in FIG. 3, curved mirrors or rotating mirrors may be used in place of, or in addition to, movable mirrors.

Returning to FIG. 2, the photodetector 208 is disposed at least partially within the housing of the mobile device 102 and can be any of a variety of sensors that can sense EM radiation, such as visible light or IR radiation, and convert the EM radiation into an electric signal that corresponds to the intensity of the EM radiation. For example, the photodetector 208 may be a photodiode, a reverse-biased LED, or a phototransistor. The photodetector 208 receives the recombined light from the interferometer 206 and outputs data that corresponds to measured light intensity of the recombined light as a function of a path length or a mirror position of the interferometer 206 (e.g., the detector data 104).

The mobile device 102 also includes or is able to communicate with a display 210, a transceiver 212, one or more processors 214, and a computer-readable storage media 216 (CRM 216). The mobile device 102 may also include one or more sensors 218 (e.g., a thermometer, or a pulse oximeter that can produce a photoplethysmogram (PPG)). In particular, the PPG may be used to synchronize the spectrum data set with pulsatile flow of the person's blood. In this way, spectra at peak blood flow and low blood flow can be distinguished, which enables a concentration of solutes in the person's blood to be distinguished from solute concentrations in the surrounding tissue.

The transceiver 212 is capable of sending and receiving data directly or through a communication network, such as detector data 104 from the mobile devices 102 through a local area, wide area, personal area, cellular, or near-field network. The processors 214 can be used to perform computing operations or functions, execute programs or applications, and so forth.

The CRM 216 includes a spectroscopy module 220 that includes, or has access to, data output from the photodetector 208 (e.g., the detector data 104). Generally, the spectroscopy module 220 represents functionality to process the detector data 104 output by the photodetector 208 to generate an interferogram. The spectroscopy module 220 can also generate a spectrum data set of the recombined light, based on the interferogram. For example, the spectroscopy module 220 can compute a Fourier transform of the interferogram (or the detector data 104) to generate a spectrum data set that describes transmission (e.g., transmittance) or reflection (e.g., reflectance) correlated with a wavelength, frequency, or wave number of the recombined light. The spectrum data set can be visually represented as a spectrum plot. Consequently, the terms spectrum data set and spectrum plot generally describe the same information (e.g., a reflectance or transmittance spectrum plot is a plot of the reflectance or transmittance spectrum data set, respectively). The spectroscopy module 220 can use an algorithm, such as a fast Fourier transform (FFT), to compute the Fourier transform of the interferogram (or the detector data) and generate either or both of the spectrum data set and the spectrum plot for reflectance or transmittance.

In some implementations, the CRM 216 may also include a pre-processing module 222 that can perform operations on the spectrum data to improve the signal-to-noise ratio in the spectrum data (e.g., reduce noise and enhance relevant or interesting features of the data). For example, the pre-processing module 222 can be used to determine absorbance, perform a background noise correction, and normalize the spectrum data.

To determine absorbance, the pre-processing module 222 can use reflectance or transmittance values for solutes at various wavelengths (e.g., from the reflectance or transmittance spectrum data sets) to determine or derive absorbance values at the various wavelengths, frequencies, or wave numbers using one or more suitable techniques. For example, the pre-processing module 222 can employ a simple equation such as $A=\log 1/R$ or $A=\log (I_0/I)$, where A is absorbance, R is reflectance, $I_o$ is the intensity of the incident light, and I is the intensity of the transmitted light. In other implementations, the pre-processing module 222 can use a more-detailed process to determine absorbance, such as a Kubelka-Munk transform. In this way, an absorbance spectrum data set (and an absorbance spectrum plot) may be generated.

The pre-processing module 222 can perform background noise correction using any of several suitable techniques, such as second-order differentiation (also called second derivative), Savitzky-Golay (SG) filtering, or a combination method, such as an SG-based second-order differentiation. Other techniques include polynomial fitting, wavelet denoising (WDN), principal component analysis (PCA), and low-pass filtering. To normalize the data, the pre-processing module 222 can use any of a variety of appropriate techniques, such as standard normal variate (SNV) normalization, multiplicative scatter correction (MSC), extended multiplicative scatter correction (EMSC), or min-max normalization.

The spectroscopy module 220 can also calculate, based on any one or more of the described spectrum data sets, a concentration of a solute in the person's blood or other tissue (e.g., intracellular fluid or extracellular fluid). The solutes can include biomolecules and metabolites such as glucose, ethanol, methemoglobin, total hemoglobin, lactate, and lipoproteins. For example, the spectroscopy module 220 can use a supervised regression technique, such as partial least squares (PLS) regression to determine solute concentrations. In implementations that use PLS regression, the spectrum data is apportioned between training data and testing data. For example, the spectrum data set can be proportioned as 70 percent training data and 30 percent testing data, 50 percent training data and 50 percent testing data, or 30 percent training data and 70 percent testing data. Other supervised regression techniques for determining solute concentration include discriminant analysis (DA), principal component regression (PCR), and multiple linear regression (MLR). In some cases, a supervised learning model, such as support vector machines (SVM), can be used to determine the solute concentration.

In some implementations, the spectroscopy module 220 can also or instead compare absorbance peaks of water in the spectrum data set to absorbance peaks of other molecules of interest to determine a proportion of those molecules versus water, which allows the spectroscopy module 220 to determine the concentration of the other molecules. Other techniques, such as the Beer-Lambert law, can also be used to determine concentrations of the solutes from the absorbance. For example, one form of the Beer-Lambert law is $A=\varepsilon l\,c$, where A is absorbance, $\varepsilon$ is molar absorptivity, l is a path length of the recombined light, and c is a concentration.

Figure 4:
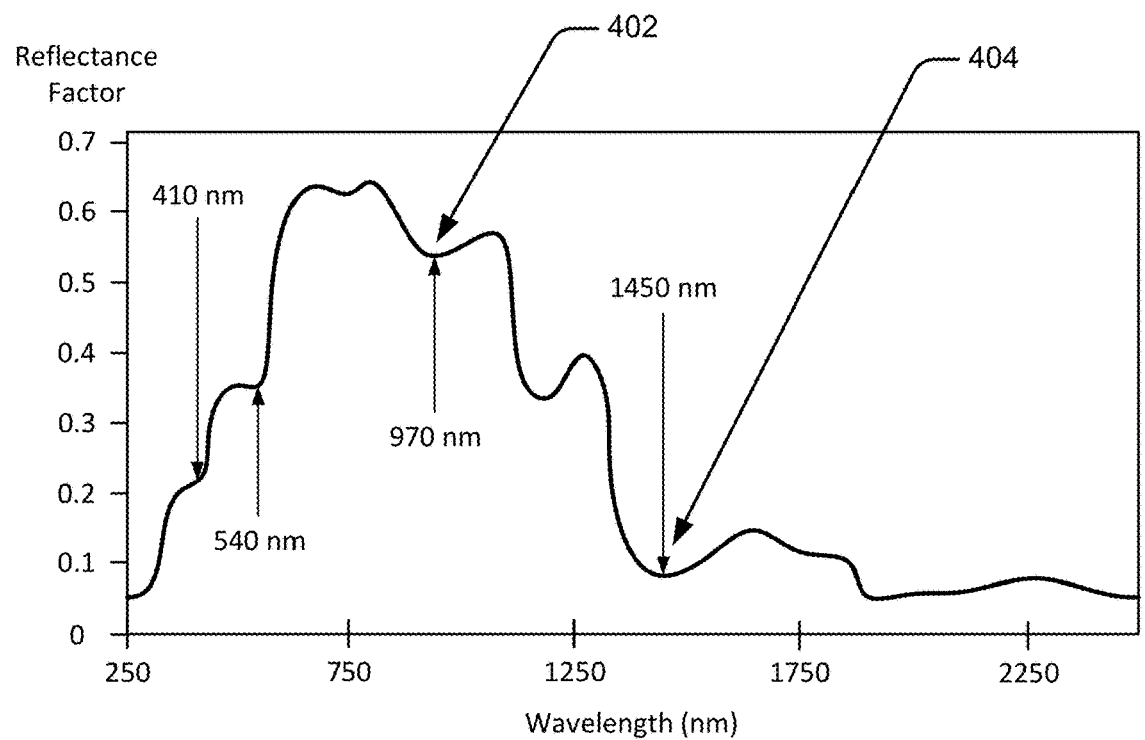
FIG. 4 illustrates a diagram of a spectrum plot based on an example spectrum data set.

Consider an example diagram 400, as shown in FIG. 4, which illustrates wavelength, in nanometers (nm), against a reflectance factor. Particular peaks and troughs of interest (410 nm, 540 nm, 970 nm, and 1450 nm), which indicate the presence of various solutes, are labeled. The techniques described above can be used to convert from reflectance (R) to absorbance (A) and perform pre-processing of the data. The PLS regression (or another technique) can then be used to determine concentrations of the solutes. Thus, a particular peak 402 indicates a calculable concentration of a solute that absorbs or reflects light at 970 nm. Similarly, another peak 404 indicates a calculable concentration of a solute that absorbs or reflects light at 1450 nm.

Returning to FIG. 2, the CRM 216 also includes or has access to a user interface 224, a machine-learning module 226, and one or more applications 228. In some implementations, any or all of the user interface 224, the machine-learning module 226, and the applications 228 may be omitted. The user interface 224 can be used to present information related to solute concentrations, such as a level of a particular solute. The machine-learning module 226 can be used to improve the performance of the mobile device 102 for FT-IR spectroscopy. For example, the machine-learning module 226 can use multiple spectrum data sets as input neurons to train a deep neural network to output a concentration of solutes in the person's blood from an input of one spectrum or multiple spectra.

The applications 228 can include programs or applications that use information about solute concentration to provide treatment or behavioral recommendations to the person. For example, an application 228 that has other information about the person can use blood-glucose concentration information to recommend whether the person should administer insulin or eat a snack. Another application 228 may use lactate concentrations to design an exercise regimen to improve endurance. The machine-learning module 226 and the applications 228 may use the display 210 to present information to the person.

Figure 5:
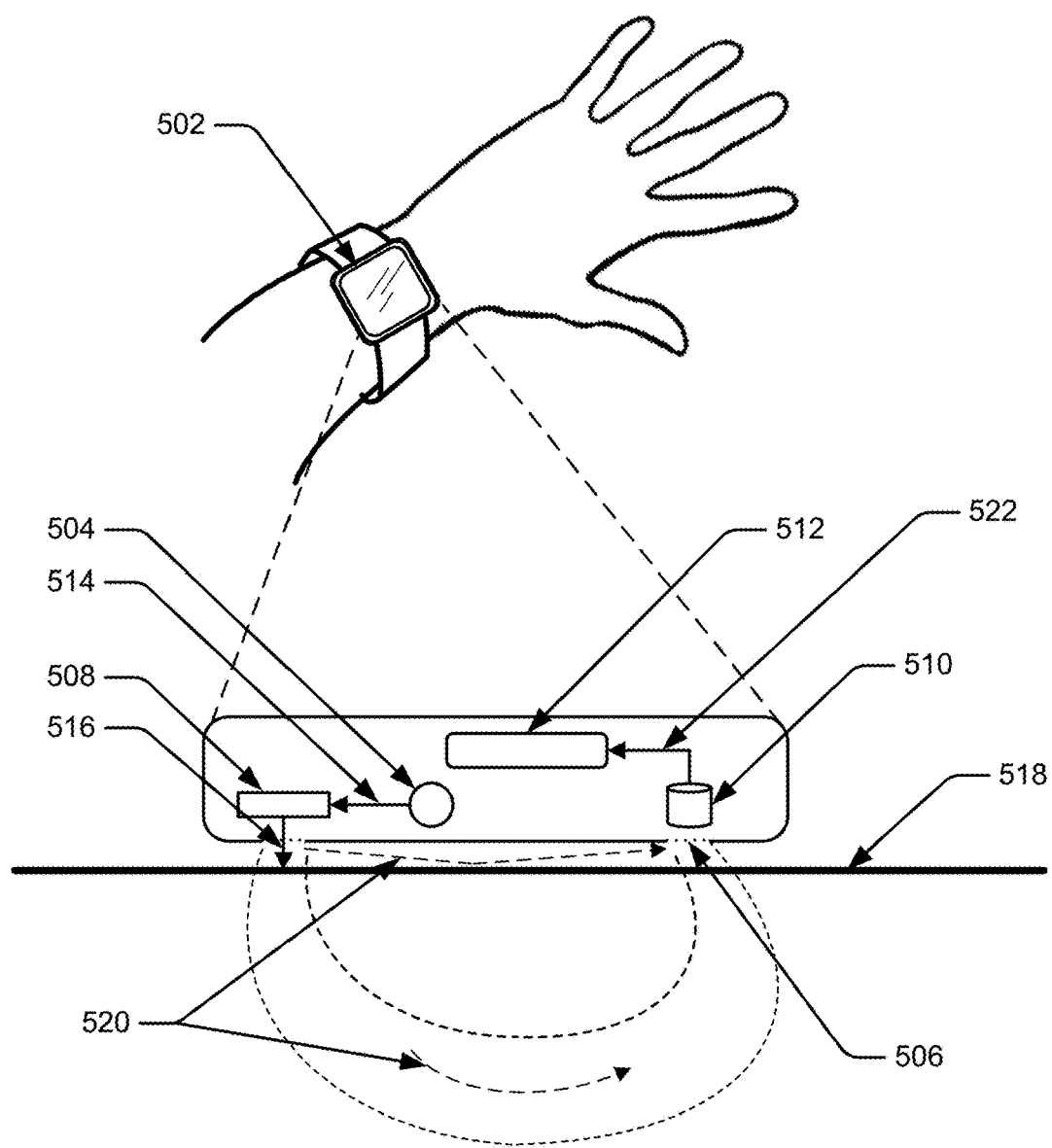
FIGS. 5-7 illustrate example implementations, including additional details, of the mobile device of FIG. 2.

FIG. 5 illustrates another example 500 of a mobile device that can implement blood-solute calculation with a mobile device using non-invasive spectroscopy. The example 500 illustrates a mobile device 502, which may be any of a variety of mobile devices (e.g., mobile devices 102-1 through 102-4). The mobile device 502 includes a light source 504 (e.g., the light source 202), a reception port 506, an interferometer 508 (e.g., the interferometer 206), a photodetector 510, and a spectroscopy module 512 (e.g., the spectroscopy module 220). Some other components of the mobile device 502, such as those described with reference to the mobile device 102, are not shown in FIG. 5.

As shown in FIG. 5, the light source 504 emits light 514 (e.g., broadband visible light and IR light, as described above) toward the interferometer 508, which splits and recombines the light (e.g., as described with respect to FIG. 2 and FIG. 3). The interferometer 508 directs recombined light 516 toward a subject 518, such as a person's skin or body. Consequently, the recombined light 516 is absorbed by, reflected from, and transmitted through the subject 518, as illustrated by arrows 520 (reflected and transmitted light 520). The reflected and transmitted light is collected through the reception port 506 into the photodetector 510.

The photodetector 510 receives the reflected and transmitted light 520 and outputs detector data 522 to the spectroscopy module 512. The detector data 522 corresponds to measured light intensity of the reflected and transmitted light 520 as a function of a path length or a mirror position of the interferometer 508 (e.g., as described with reference to FIG. 2 and FIG. 3). As described with reference to FIGS. 2-4, the spectroscopy module 512 can generate an interferogram based on the detector data 522 and generate a spectrum data set (e.g., a reflectance spectrum data set or a transmittance spectrum data set) of the reflected and transmitted light 520 based on the interferogram. Based on the spectrum data set, the spectroscopy module 512 can determine concentrations of various solutes in the person's blood and provide the results to the person or another entity.

Figure 6:
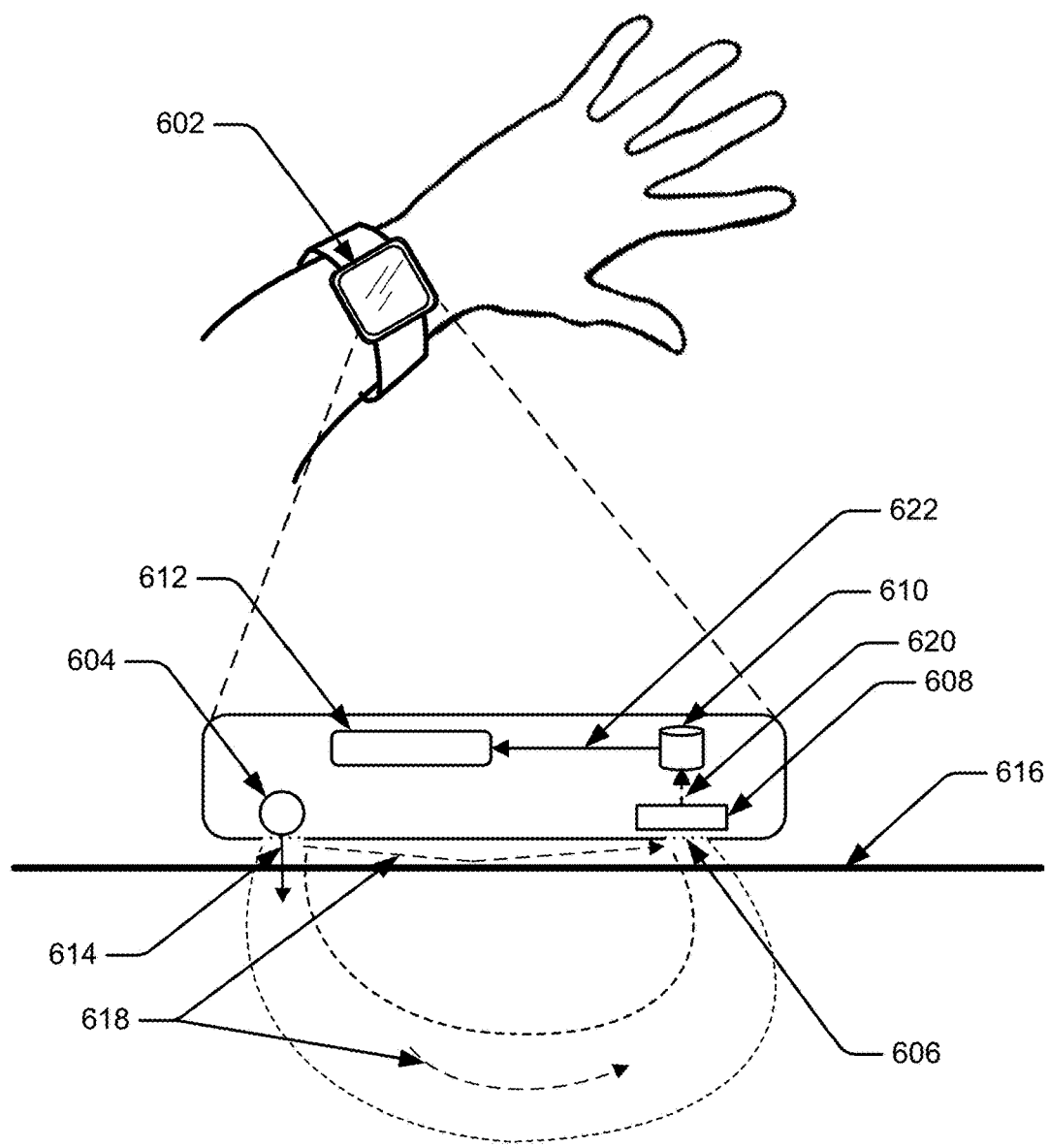

FIG. 6 illustrates another example 600 of a mobile device that can implement blood-solute calculation with a mobile device using non-invasive spectroscopy. The example 600 illustrates a mobile device 602, which may be any of a variety of mobile devices (e.g., mobile devices 102-1 through 102-4). The mobile device 602 includes a light source 604 (e.g., the light source 202), a reception port 606 (e.g., the reception port 204), an interferometer 608 (e.g., the interferometer 206), a photodetector 610, and a spectroscopy module 612 (e.g., the spectroscopy module 220). Some other components of the mobile device 602, such as those described with reference to the mobile device 102, are not shown in FIG. 6.

As shown in FIG. 6, the light source 604 emits light 614 toward a subject 616 (e.g., the skin of a person). The emitted light 614 is absorbed, reflected, and transmitted by the subject 616, as illustrated by arrows 618 (reflected and transmitted light 618). The reflected and transmitted light 618 is collected through the reception port 606 into the interferometer 608. The interferometer 608 splits and recombines the light (e.g., as described with respect to FIG. 2 and FIG. 3) and directs the recombined light 620 toward the photodetector 610.

The photodetector 610 receives the recombined light 620 and outputs detector data 622 to the spectroscopy module 612. The detector data 622 corresponds to measured light intensity of the recombined light 620 as a function of a path length or a mirror position of the interferometer 608 (e.g., as described with reference to FIG. 2 and FIG. 3). As described with reference to FIG. 2 through FIG. 4, the spectroscopy module 612 can generate an interferogram based on the detector data 622 and generate a spectrum data set of the recombined light 620 (e.g., a reflectance spectrum data set or a transmittance spectrum data set) based on the interferogram. Based on the spectrum data set, the spectroscopy module 612 can determine concentrations of various solutes in the person's blood and provide the results to the person or another entity.

Figure 7:
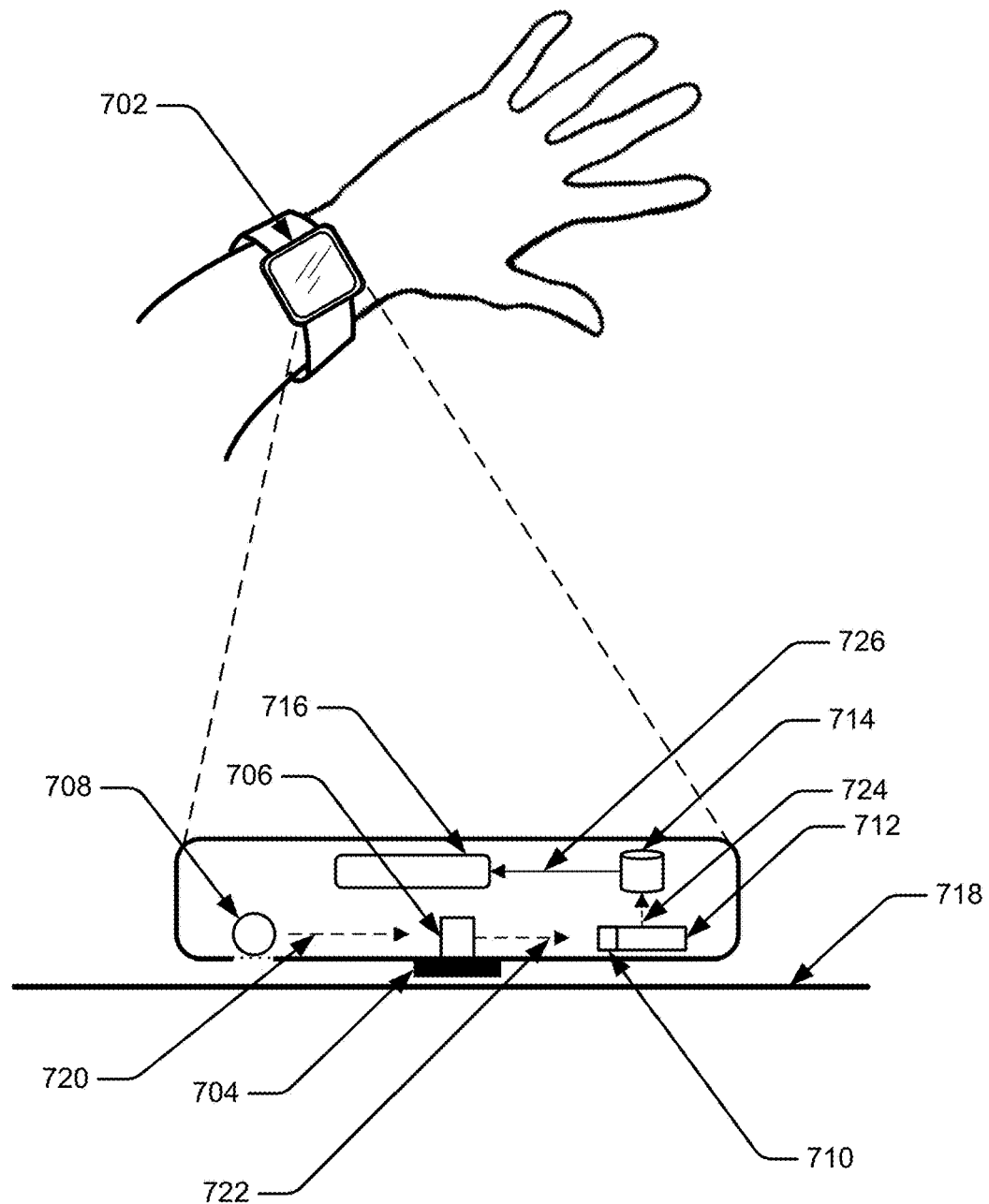

FIG. 7 illustrates yet another example 700 of a mobile device that can implement blood-solute calculation with a mobile device using non-invasive spectroscopy. The example 700 illustrates a mobile device 702, which may be any of a variety of mobile devices (e.g., mobile devices 102-1 through 102-4). The mobile device 702 includes a wicking medium 704, a sample collection area 706, a light source 708, a reception port 710, an interferometer 712, a photodetector 714, and a spectroscopy module 716. Some other components of the mobile device 702, such as those described with reference to the mobile device 102, are not shown in FIG. 7. The wicking medium 704 may be made from a variety of materials that can absorb perspiration from a person's skin 718 and collect the perspiration at the sample collection area 706 (e.g., by capillary action, or a "wicking" process). For example, the wicking medium 704 may be made from a variety of polyesters, nylons, or polypropylenes. The wicking medium 704 and the sample collection area 706 can be separate components or a single component. Either or both of the wicking medium 704 and the sample collection area 706 may be reusable or disposable and replaceable.

The light source 708, the reception port 710, the interferometer 712, the photodetector 714, and the spectroscopy module 716 may be similar to corresponding items described with reference to FIG. 2 (e.g., the light source 202, the reception port 204, the interferometer 206, the photodetector 208, and the spectroscopy module 220). As shown in FIG. 7, the light source 708 emits light 720 toward the sample collection area 706. The emitted light 720 is absorbed by, reflected from, and transmitted by the perspiration in the sample collection area 706. The reflected and transmitted light, as shown by arrow 722, is collected through the reception port 710 into the interferometer 712. The interferometer 712 splits and recombines the light (e.g., as described with respect to FIG. 2 and FIG. 3) and directs the recombined light 724 toward the photodetector 714.

The photodetector 714 receives the recombined light 724 and outputs detector data 726 to the spectroscopy module 716. The detector data 726 corresponds to measured light intensity of the recombined light 724 as a function of a path length or a mirror position of the interferometer 712 (e.g., as described with reference to FIG. 2 and FIG. 3). As described with reference to FIG. 2 through FIG. 4, the spectroscopy module 716 can generate an interferogram based on the detector data 726, and generate a spectrum data set (e.g., a reflectance spectrum data set or a transmittance spectrum data set) of the recombined light based on the interferogram. Based on the spectrum data set, the spectroscopy module 716 can determine concentrations of various solutes in the person's perspiration and provide the results to the person or another entity.

These and other capabilities, as well as ways in which entities of FIG. 1 through FIG. 7 act and interact, are set forth in greater detail below. These entities may be further divided, combined, and so on. The environment 100 of FIG. 1 and the detailed illustrations of FIG. 2 through FIG. 7 illustrate some of many possible environments capable of employing the described techniques.

Example Methods

FIGS. 8-11 depict methods enabling or implementing blood-solute calculation with a mobile device using non-invasive spectroscopy. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIG. 2 through FIG. 7, reference to which is made for the purpose of example. The techniques are not limited to performance by one entity or multiple entities operating on one device.

Figure 8:
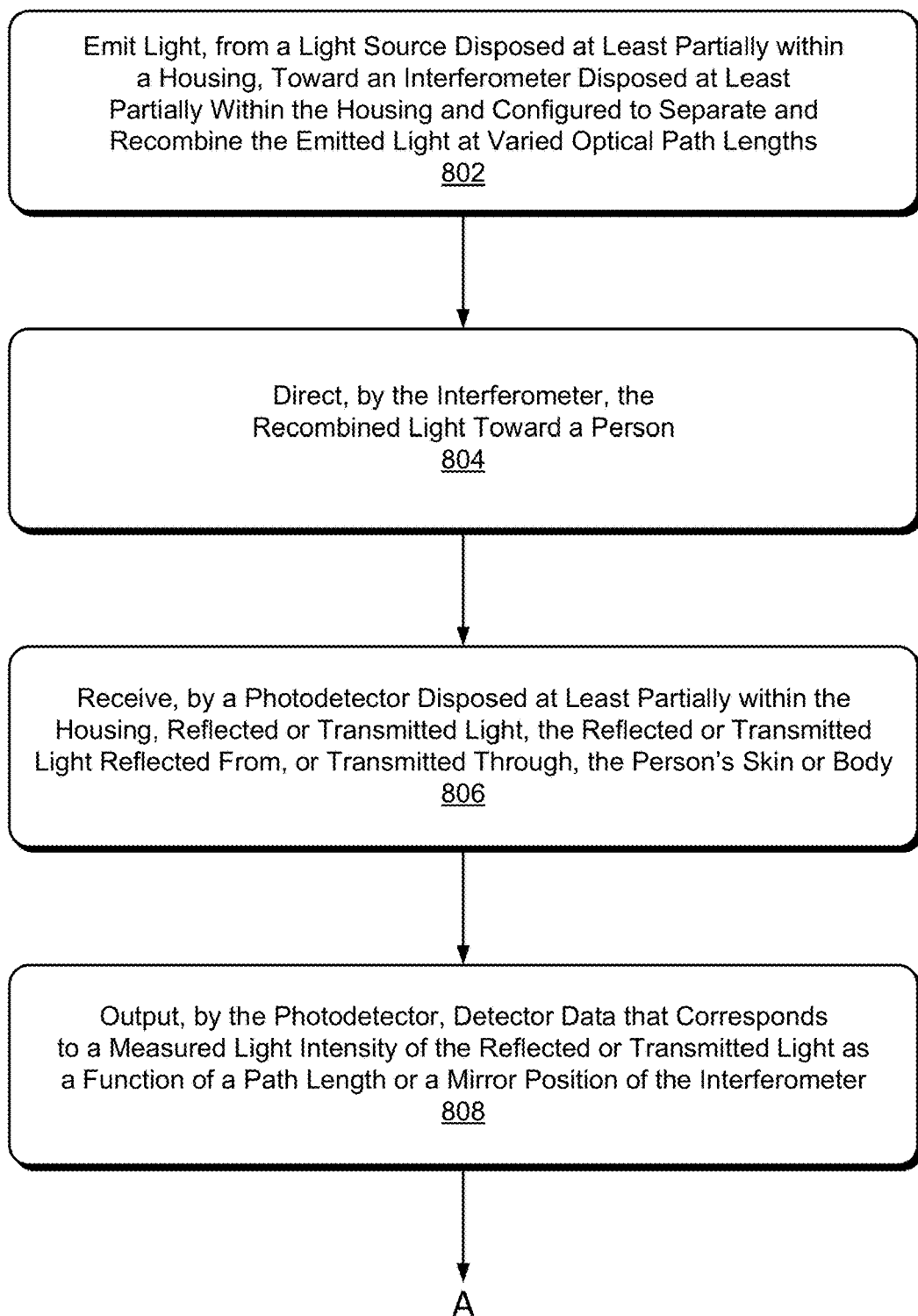
FIGS. 8-11 depict example methods enabling blood-solute calculation with a mobile device using non-invasive spectroscopy.
Figure 9:
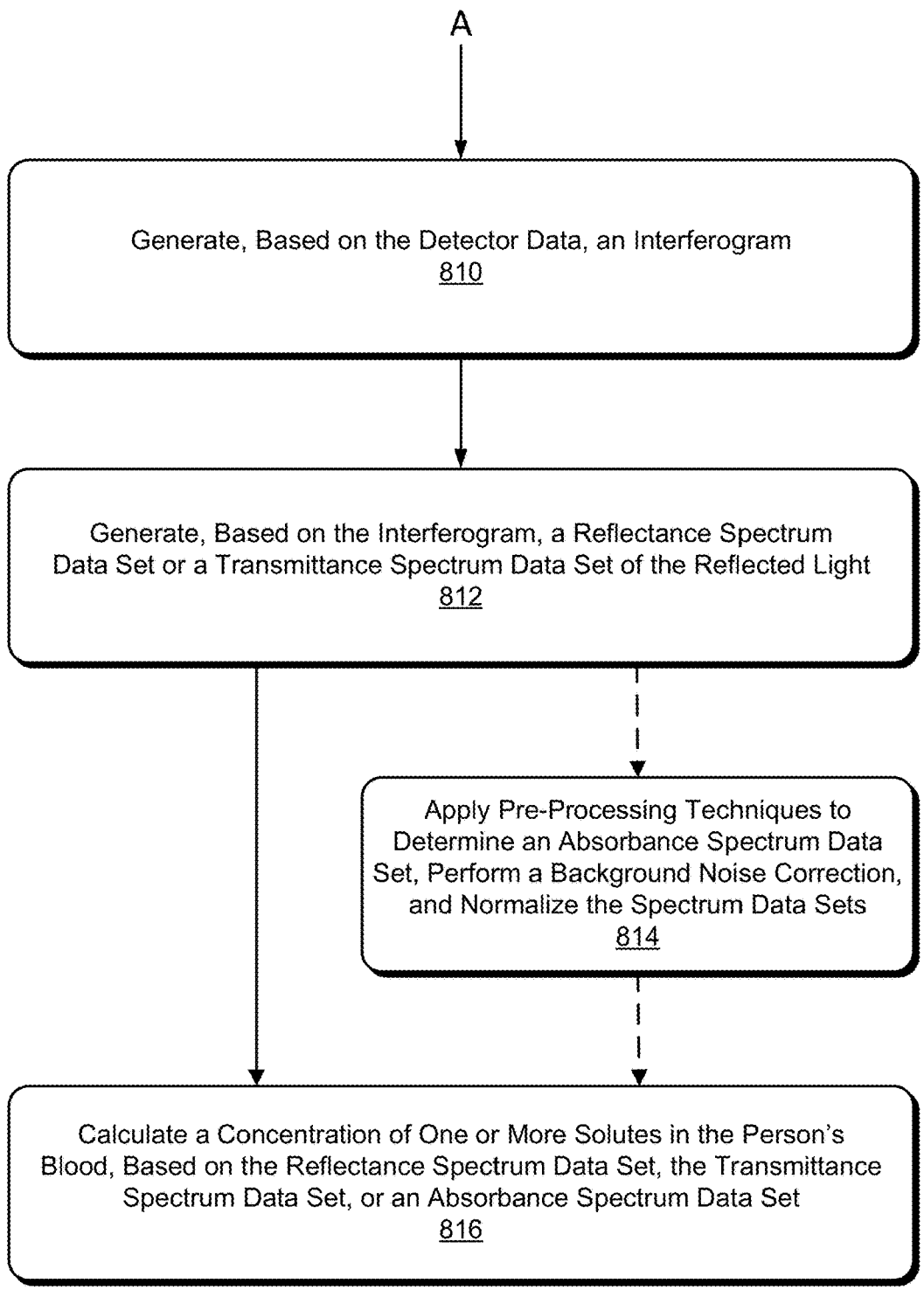

FIG. 8 and FIG. 9 depict a method 800, which describes techniques that enable blood-solute calculation with a mobile device using non-invasive spectroscopy. At 802, light is emitted from a light source disposed at least partially within a housing toward an interferometer disposed at least partially within the housing. The light source can be a variety of light sources that can emit broadband visible light and infrared (IR) light (e.g., the light source 202). The interferometer separates and recombines the emitted light. For example, the interferometer may be the interferometer 206 or another interferometer, such as the example Michelson and Fabry-Perot interferometers described with reference to FIG. 3.

At 804, the interferometer directs the recombined light toward a subject, such as a person's skin or body. For example, as shown in FIG. 3, a Michelson interferometer may use a beam-splitter to recombine the emitted light and direct the recombined beam out of the interferometer. A Fabry-Perot interferometer, in contrast, may use a focusing lens to recombine and direct the emitted light out of the interferometer. In this way, the interferometer can separate and recombine the light at a varied optical path lengths.

At 806, a photodetector disposed at least partially within the housing receives reflected light. The reflected light is light from the light source that is reflected from, or transmitted through, the subject. The photodetector can be any suitable sensor that can sense EM radiation and convert the EM radiation into an electric signal that corresponds to the intensity of the EM radiation, such as the photodetector 208.

At 808, the photodetector outputs detector data that corresponds to a measured light intensity of the reflected light as a function of a path length or a mirror position of the interferometer. For example, the detector data may be the detector data 104. The description of the method 800 continues at FIG. 9, as indicated by the letter "A" after block 808 of FIG. 8, which corresponds to the letter "A" before block 810 of FIG. 9.

At 810, an interferogram is generated, based on the detector data. For example, a spectroscopy module (e.g., one or more of the spectroscopy modules 220, 512, 612, or 716) can be used to generate the interferogram.

At 812, a spectrum data set of the reflected light is generated, based on the interferogram. For example, the spectroscopy module described with reference to block 812 can use an algorithm, such as a fast Fourier transform (FFT) to compute the Fourier transform of the interferogram. A spectrum data set of transmittance or reflectance (e.g., a transmittance spectrum data set or a reflectance spectrum data set) can be generated using the Fourier transform. The spectrum data sets describe a relationship between reflectance or transmittance and wavelength, frequency, or wave number of the reflected light.

Optionally, at 814, pre-processing techniques can be applied to the transmittance spectrum data set, the reflectance spectrum data set (e.g., reflectance or transmittance spectrum data), or an absorbance spectrum data set. The pre-processing techniques can be used, for example, to determine absorbance, perform a background noise correction, and normalize the spectrum data sets. As described with reference to FIG. 2, absorbance can be determined using a simple equation such as A=log 1/R or A=log ($I_0$/I). In other cases, a more-detailed process, such as a Kubelka-Munk transform, can be used to determine absorbance. In this way, the absorbance spectrum data set may be generated.

The background noise correction can be applied to any one or more of the described spectrum data sets using any suitable technique, such as second-order differentiation (also called second derivative), Savitzky-Golay (SG) filtering, or a combination method, such as an SG-based second-order differentiation, as described with reference to FIG. 2. To normalize the spectrum data sets, any of a variety of appropriate techniques, such as standard normal variate (SNV) normalization or multiplicative scatter correction (MSC) may be applied.

At 816, based on the absorbance spectrum data set, the reflectance spectrum data set, or the transmittance spectrum data set, a concentration of one or more solutes in the person's blood or other tissue (e.g., intracellular fluid or extracellular fluid) is calculated. In some implementations, the concentration can be calculated using a suitable supervised regression technique, such as partial least squares (PLS) regression. In some cases, a supervised learning model, such as support vector machines (SVM), can be used to determine the solute concentration.

Figure 10:
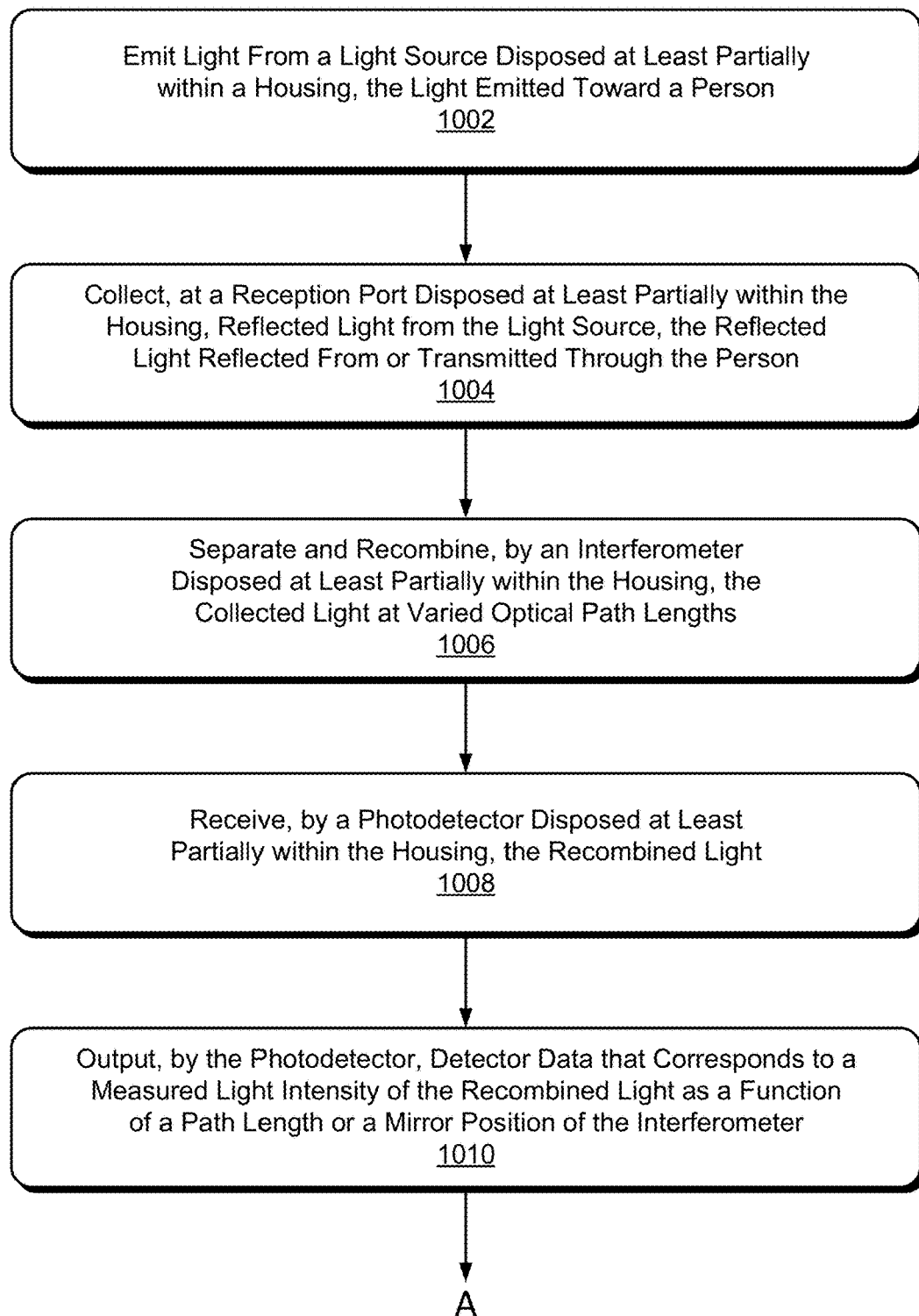
Figure 11:
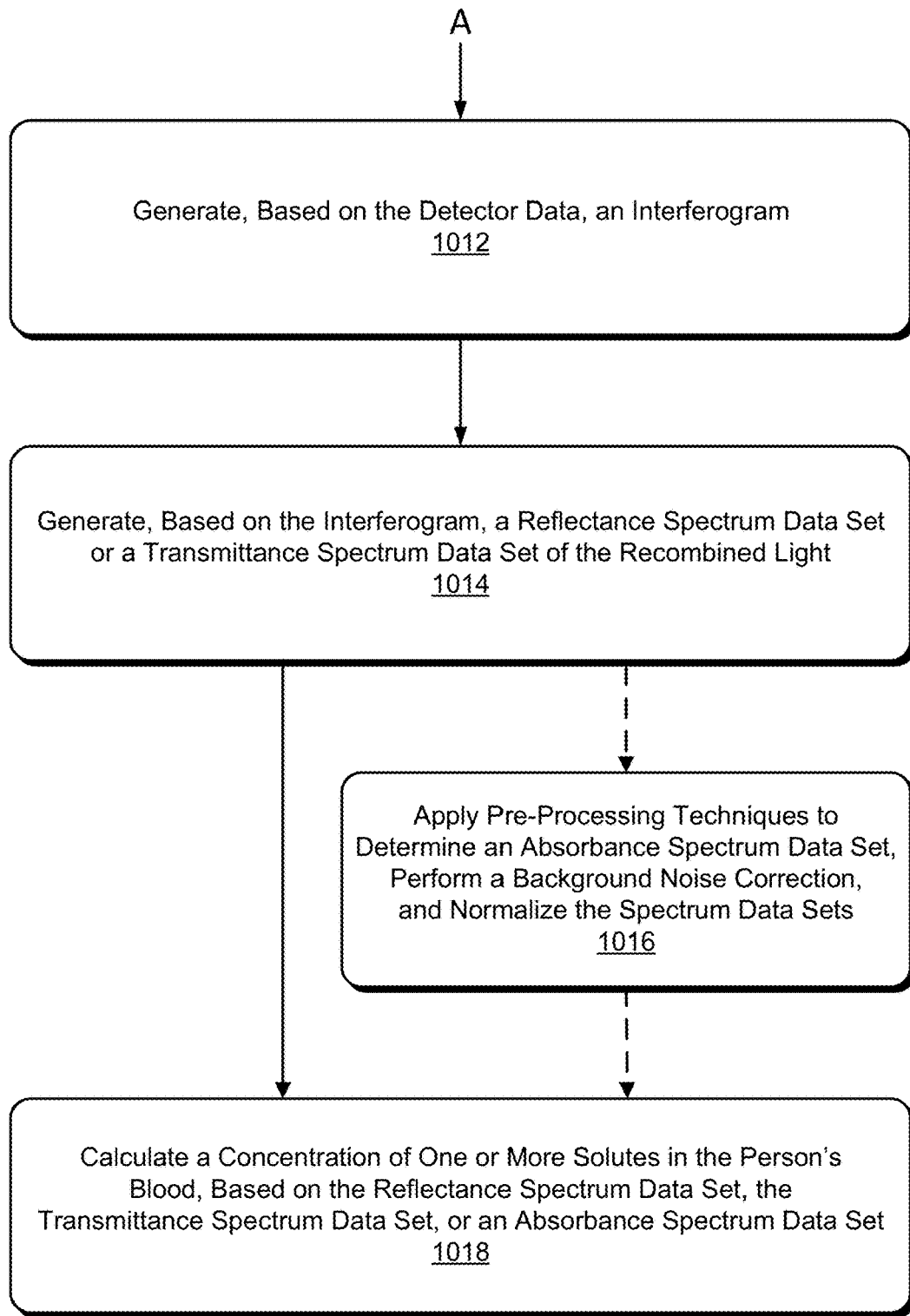

FIG. 10 depicts another method 1000, which describes techniques that enable blood-solute calculation with a mobile device using non-invasive spectroscopy. At 1002, light is emitted toward a subject (e.g., a person) from a light source disposed at least partially within a housing of a mobile device, such as the mobile device 102, 502, 602, or 702, as described with reference to earlier figures. The light source can be a variety of light sources that can emit broadband visible light and infrared (IR) light (e.g., the light source 202).

At 1004, a reception port disposed at least partially within the housing collects reflected light from the light source. The reflected light is light that is reflected from or transmitted through the subject. The reception port may be, for example, the reception port 204 as described with reference to FIG. 2.

At 1006, an interferometer disposed at least partially within the housing receives the collected light through the reception port. The interferometer separates and recombines the collected light. For example, the interferometer may be the interferometer 206 or another interferometer, such as the example Michelson and Fabry-Perot interferometers described with reference to FIG. 3.

At 1008, a photodetector disposed at least partially within the housing, receives the recombined light from the interferometer. The photodetector can be any of a variety of sensors that can sense EM radiation and convert the EM radiation into an electric signal that corresponds to the intensity of the EM radiation, such as the photodetector 208 described with reference to FIG. 2.

At 1010, the photodetector outputs detector data that corresponds to a measured light intensity of the recombined light as a function of a path length or a mirror position of the interferometer. For example, the detector data may be the detector data 104 described with reference to FIG. 1 and FIG. 2. The description of the method 1000 continues at FIG. 11, as indicated by the letter "A" after block 1010 of FIG. 10, which corresponds to the letter "A" before block 1012 of FIG. 11.

At 1012, an interferogram is generated, based on the detector data. For example, a spectroscopy module (e.g., one or more of the spectroscopy modules 220, 512, 612, or 716) can be used to generate the interferogram.

At 1014, a spectrum data set of the recombined light is generated, based on the interferogram. For example, the spectroscopy module described with reference to block 1012 can use an algorithm, such as a fast Fourier transform (FFT) to compute the Fourier transform of the interferogram. A spectrum data set of transmittance or reflectance (e.g., a transmittance spectrum data set or a reflectance spectrum data set) can be generated using the Fourier transform. The spectrum data sets describe a relationship between transmittance or reflectance and wavelength, frequency, or wave number of the recombined light.

Optionally, at 1016, pre-processing techniques can be applied to the transmittance spectrum data set, the reflectance spectrum data set (e.g., reflectance or transmittance spectrum data), or an absorbance spectrum data set. The pre-processing techniques can be used, for example, to determine absorbance, perform a background noise correction, and normalize the spectrum data sets. As described with reference to FIG. 2, absorbance can be determined using a simple equation such as $A=\log 1/R$ or $A=\log (I_0/I)$. In other cases, a more-detailed process, such as a Kubelka-Munk transform, can be used to determine absorbance. In this way, the absorbance spectrum data set may be generated.

The background noise correction can be applied to any one or more of the described spectrum data sets using any suitable technique, such as second-order differentiation (also called second derivative), Savitzky-Golay (SG) filtering, or a combination method, such as an SG-based second-order differentiation, as described with reference to FIG. 2. To normalize the spectrum data sets, any of a variety of appropriate techniques, such as standard normal variate (SNV) normalization or multiplicative scatter correction (MSC) may be applied.

At 1018, based on the absorbance spectrum data set, the reflectance spectrum data set, or the transmittance spectrum data set, a concentration of one or more solutes in the person's blood or other tissue (e.g., intracellular fluid or extracellular fluid) is calculated. In some implementations, the concentration can be calculated using a suitable supervised regression technique, such as partial least squares (PLS) regression. In some cases, a supervised learning model, such as support vector machines (SVM), can be used to determine the solute concentration.

As noted, multiple spectrum data sets (including the absorbance spectrum data set, the reflectance spectrum data set, or the transmittance spectrum data set) can be used as input neurons to train a deep neural network to output a concentration of a solute in the person's blood, based on an input of one spectrum or multiple spectra. Some of the solutes for which concentrations can be determined include biomolecules and metabolites such as glucose, hemoglobin, lactate, and alcohol.

Example Electronic Device

Figure 12:
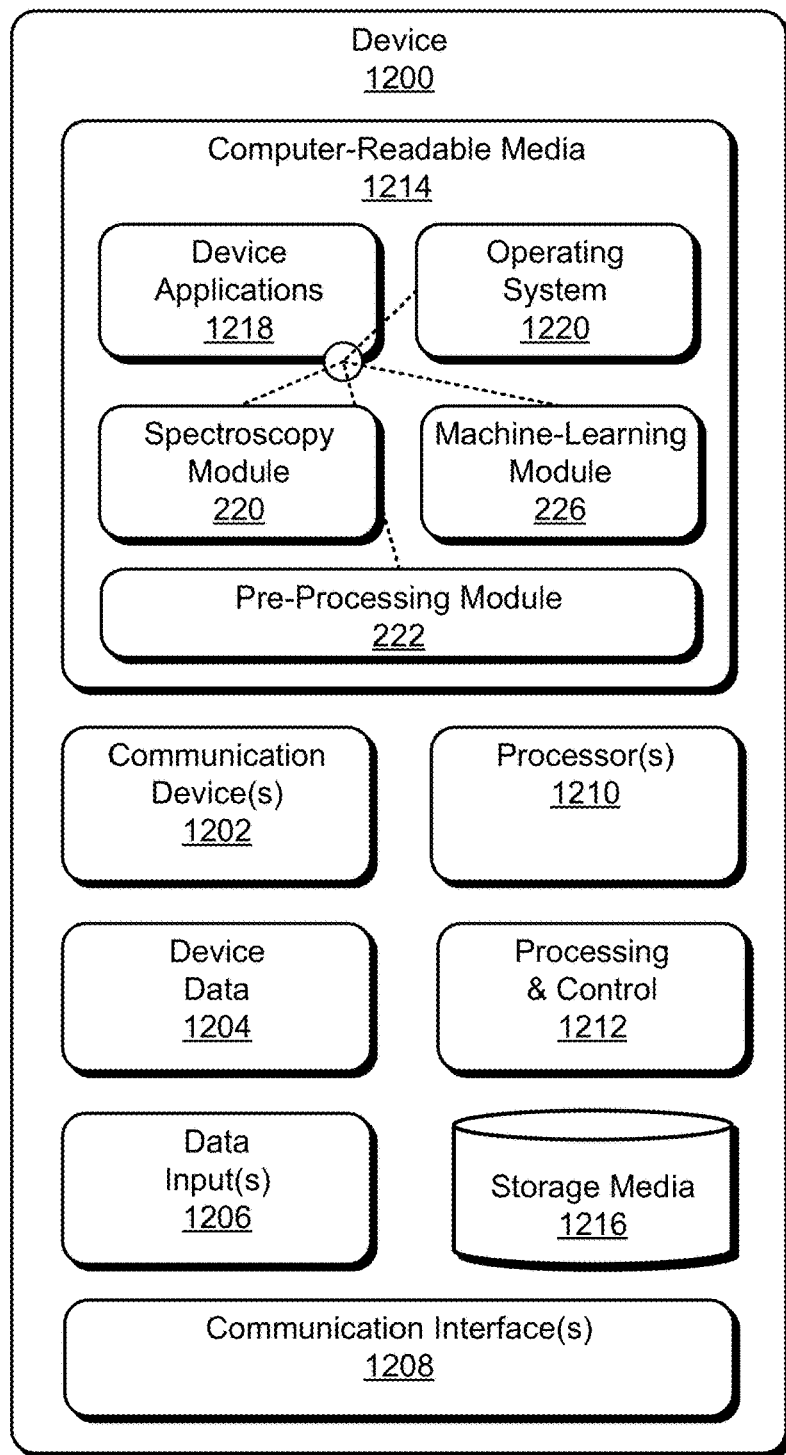
FIG. 12 illustrates various components of an example mobile device that can be implemented as any type of client, server, and/or electronic device as described with reference to FIG. 1-11 to implement, or in which techniques may be implemented that enable, blood-solute calculation with a mobile device using non-invasive spectroscopy.

FIG. 12 illustrates various components of an example device 1200 (device 1200) that can be implemented as any type of client, server, and/or computing device as described with reference to the previous FIGS. 1-11 to implement blood-solute calculation with a mobile device using non-invasive spectroscopy.

The device 1200 includes communication devices 1202 that enable wired and/or wireless communication of device data 1204 (e.g., photodetector data, spectrum data, received data, data that is being received, data scheduled for broadcast, data packets of the data, etc.). The device data 1204 or other device content can include configuration settings of the device, media content stored on the device, and/or information associated with a user of the device (e.g., measurements of concentrations of one or more solutes in the user's blood or perspiration). Media content stored on the device 1200 can include any type of spectrum, audio, video, and/or image data. The device 1200 includes one or more data inputs 1206 via which any type of data, media content, and/or inputs can be received, such as light or other EM radiation, human utterances, interactions with a radar field, user-selectable inputs (explicit or implicit), messages, music, television media content, recorded video content, and any other type of audio, video, and/or image data received from any content and/or data source. The data inputs 1206 may include, for example, the photodetector 208, the spectroscopy module 220, the pre-processing module 222, or the machine-learning module 226.

The device 1200 also includes one or more communication interfaces 1208, which can be implemented as any one or more of a serial and/or parallel interface, a wireless interface, any type of network interface, a modem, and as any other type of communication interface. The communication interfaces 1208 provide a connection and/or communication links between the device 1200 and a communication network by which other electronic, computing, and communication devices communicate data with the device 1200.

The device 1200 includes one or more processors 1210 (e.g., any of microprocessors, controllers, and so forth), which process various computer-executable instructions to control the operation of the device 1200 and to enable techniques for, or in which can be embodied, blood-solute calculation with a mobile device using non-invasive spectroscopy. Alternatively or in addition, the device 1200 can be implemented with any one or combination of hardware, firmware, or fixed logic circuitry that is implemented in connection with processing and control circuits which are generally identified at 1212. Although not shown, the device 1200 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

The device 1200 also includes computer-readable media 1214, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. The disk storage device may be implemented as any type of magnetic or optical storage device, such as a hard disk drive, a recordable and/or rewritable compact disc (CD), any type of a digital versatile disc (DVD), and the like. The device 1200 can also include a mass storage media device (storage media) 1216.

The computer-readable media 1214 provides data storage mechanisms to store device data 1204, as well as various device applications 1218 and any other types of information and/or data related to operational aspects of the device 1200. For example, an operating system 1220 can be maintained as a computer application with computer-readable media 1214 and executed on the processors 1210. The device applications 1218 may include a device manager, such as any form of a control application, software application, signal-processing and control module, code that is native to a particular device, a hardware abstraction layer for a particular device, and so on. The device applications 1218 also include system components, engines, modules, or managers to implement blood-solute calculation with a mobile device using non-invasive spectroscopy, such as the spectroscopy module 220, the pre-processing module 222, and the machine-learning module 226.

CONCLUSION

Although embodiments of techniques enabling blood-solute calculation with a mobile device using non-invasive spectroscopy have been described in language specific to features and/or methods, it is to be understood that the subject of the appended claims is not necessarily limited to the specific features or methods described. Rather, the specific features and methods are disclosed as example implementations of ways in which to perform blood-solute calculation with a mobile device using non-invasive spectroscopy.

What is claimed is:

1. A method comprising:
   emitting light from a light source toward an interferometer;
   directing the light, by the interferometer, toward a person;
   receiving, by a photodetector, reflected or transmitted light, the reflected or transmitted light reflected from, or transmitted through, the person;
   outputting, by the photodetector, detector data that corresponds to a measured light intensity of the reflected or transmitted light;
   generating, based on the detector data, a reflectance spectrum data set or a transmittance spectrum data set of the received light;
   generating, based on the reflectance spectrum data set or the transmittance spectrum data set, an absorbance spectrum data set;
   performing a background noise correction on the absorbance spectrum data set to provide a background-noise-corrected absorbance spectrum data set; and
   calculating a concentration of one or more solutes inside the person's body, based on the background-noise-corrected absorbance spectrum data set.

2. The method of claim 1, further comprising:
   calculating a concentration of one or more solutes in the person's blood, based on the background-noise-corrected absorbance spectrum data set; or
   calculating a concentration of one or more solutes in interstitial fluid inside the person's body, based on the background-noise-corrected absorbance spectrum data set.

3. The method of claim 1, further comprising:
   performing a normalization algorithm on the background-noise-corrected absorbance spectrum data set to correct shifting and/or scaling effects introduced to the absorbance spectrum data set.

4. The method of claim 1, wherein:
   directing the light, by the interferometer, toward the person further comprises:
   separating and recombining the emitted light at varied optical path lengths; and
   directing the recombined light toward the person.

5. The method of claim 1, wherein emitting the light from the light source further comprises emitting light that includes wavelengths between approximately 100 nanometers (nm) and approximately 6000 nm.

6. The method of claim 1, wherein emitting the light from the light source further comprises emitting the light from at least one of:
   a laser;
   a light-emitting-diode (LED);
   a laser diode; or
   an array that includes one or more of diodes, laser diodes, or lasers.

7. The method of claim 1, wherein outputting, by the photodetector, detector data that corresponds to a measured light intensity of the reflected or transmitted light further comprises:
   outputting, by the photodetector, detector data that corresponds to a measured light intensity of the reflected or transmitted light as a function of a path length or a mirror position of the interferometer.

8. The method of claim 7, wherein outputting, by the photodetector, detector data that corresponds to a measured light intensity of the reflected or transmitted light further comprises:
   generating, based on the detector data, interferogram data.

9. The method of claim 8, wherein generating the reflectance spectrum data set or the transmittance spectrum data set further comprises:
   computing a Fourier transform of the interferogram data.

10. A mobile computing device comprising:
    a light source disposed at least partially within a housing and configured to emit light;
    an interferometer disposed at least partially within the housing and configured to direct the light toward a person;
    a reception port disposed at least partially within the housing and configured to collect light reflected from, or transmitted through, the person;
    a photodetector disposed at least partially within the housing and configured to:
    receive the reflected or transmitted light; and
    output detector data that corresponds to measured light intensity of the received light; and
    a spectroscopy module configured to:
    generate, based on the detector data, a reflectance spectrum data set or a transmittance spectrum data set of the received light; and
    calculate a concentration of one or more solutes inside the person's body based on a background-noise-corrected absorbance spectrum data set, the background-noise-corrected absorbance spectrum data set corrected for background noise and generated based on:
    the reflectance spectrum data set; or
    the transmittance spectrum data set.

11. The mobile computing device of claim 10, wherein:
    the interferometer is a micro-electro-mechanical systems (MEMS) interferometer configured to:
    receive the emitted light;
    separate and recombine the emitted light at varied optical path lengths; and
    direct the recombined light toward the person.

12. The mobile computing device of claim 10, wherein the spectroscopy module is further configured to:
    calculate a concentration of one or more solutes in the person's blood, based on the background-noise-corrected absorbance spectrum data set; or
    calculate a concentration of one or more solutes in interstitial fluid inside the person's body, based on the background-noise-corrected absorbance spectrum data set.

13. The mobile computing device of claim 10, further comprising a pre-processing module configured to:
    generate an absorbance spectrum data set of the received light based on:
    the reflectance spectrum data set; or
    the transmittance spectrum data set;

perform the correction for background noise on the absorbance spectrum data set to generate the background-noise-corrected absorbance spectrum data set; and perform a normalization algorithm on the absorbance spectrum data set to correct shifting and/or scaling effects introduced to the absorbance spectrum data set.

14. The mobile computing device of claim 10, wherein the light source is further configured to emit light that includes wavelengths between approximately 100 nanometers (nm) and approximately 6000 nm.

15. The mobile computing device of claim 10, wherein the light source comprises:
- a laser;
- a light-emitting-diode (LED);
- a laser diode; or
- an array that includes one or more of diodes, laser diodes, or lasers.

16. The mobile computing device of claim 10, further comprising a machine-learning module configured to use multiple spectrum data sets as input neurons to train a deep neural network to output a concentration of solutes inside the person's body from an input of one spectrum data set or multiple spectrum data sets.

17. The mobile computing device of claim 10, wherein the spectroscopy module is further configured to calculate the concentrations of the one or more solutes by performing a partial least squares regression analysis.

18. The mobile computing device of claim 10, wherein the photodetector is further configured to output the detector data that corresponds to measured light intensity of the received light as a function of a path length or a mirror position of the interferometer.

19. The mobile computing device of claim 10, wherein the spectroscopy module is further configured to:
generate, based on the detector data, interferogram data.

20. The mobile computing device of claim 19, wherein the spectroscopy module is further configured to:
generate the reflectance spectrum data set or the transmittance spectrum data set of the received light, based on the interferogram data.

* * * * *